(12) United States Patent
Scohy et al.

(10) Patent No.: US 7,910,298 B2
(45) Date of Patent: Mar. 22, 2011

(54) METHOD FOR A (HIGH THROUGH-PUT) SCREENING DETECTION OF GENETIC MODIFICATIONS IN GENOME ENGINEERING

(75) Inventors: Sophie Scohy, Nivelles (BE); Philippe Gabant, Brussels (BE); Thierry Van Reeth, Carnieres (BE)

(73) Assignee: Immunehealth, Charleroi (BE)

(*) Notice: Subject to any disclaimer, the term of this patent is extended or adjusted under 35 U.S.C. 154(b) by 980 days.

(21) Appl. No.: 11/287,053

(22) Filed: Nov. 25, 2005

(65) Prior Publication Data
US 2006/0123491 A1    Jun. 8, 2006

Related U.S. Application Data

(60) Provisional application No. 60/631,005, filed on Nov. 24, 2004.

(30) Foreign Application Priority Data

Apr. 28, 2005   (EP) ..................................... 05447099
Nov. 24, 2005   (BE) ................. PCT/BE2005/000171

(51) Int. Cl.
*C12Q 1/68*     (2006.01)
*C12N 15/63*    (2006.01)
*C12N 15/11*    (2006.01)

(52) U.S. Cl. .......................... 435/6; 435/320.1; 536/23.1
(58) Field of Classification Search ........................ None
See application file for complete search history.

(56) References Cited

U.S. PATENT DOCUMENTS

2004/0214222 A1 * 10/2004 Burgess et al. .................. 435/6

OTHER PUBLICATIONS

Ding et al., "Quantitative Analysis of Nucleic Acids—the Last Few Years of Progress," *Journal of Biochemistry and Molecular Biology*, vol. 37, No. 1, Jan. 24, pp. 1-10.
Norton et al., "Universal, robust, highly quantitative SNP allele frequency measurement DNA pools," *Hum. Genet.* (2002) 110:471-478.

* cited by examiner

*Primary Examiner* — Michele K Joike
(74) *Attorney, Agent, or Firm* — Knobbe Martens Olson & Bear, LLP (57) ABSTRACT

The present invention is related to a method for a high through-put screening detection of genetic modifications in genome engineering and a system for homologous recombination of an exogenous nucleotide sequence into a target cell genome sequence.

12 Claims, 6 Drawing Sheets

METHOD FOR A (HIGH THROUGH-PUT) SCREENING DETECTION OF GENETIC MODIFICATIONS IN GENOME ENGINEERING

RELATED APPLICATIONS

This application is a non-provisional of and claims priority to U.S. Provisional Patent Application Ser. No. 60/631,005, entitled Utilisation de methodes quantitatives developpees pour la detection de SNP pour le criblage a haut rendement d'evenements de recombinaison homologue en ingenierie de genome, filed Nov. 24, 2004, and also claims priority to EP 05447099.2, filed Apr. 28, 2005 and is a continuation of PCT Application No. PCT/BE2005/000171, filed Nov. 24, 2005, the disclosures of which are incorporated herein by reference in their entireties.

BACKGROUND OF THE INVENTION

1. Field of the Invention

The present invention is related to a method for a (high through-put) screening detection of genetic modifications in engineering genome applied upon prokaryote and eukaryote cells or organism and a method for the monitoring of these genetic modifications through generations.

2. Description of the Related Art

In order to characterize the function of genetic sequences or for modulating the activity of genetic sequences, it is important to obtain introduction of genetic modifications into these sequences present in a cell genome. By the analysis of the defect (or advantage) induced by the genetic modification (the phenotype) the function of the gene can be identified.

This new approach has been developed in the field of molecular biology of prokaryote or eukaryote cells under the term "genome engineering". This technique also applies for the production of genetically modified cells dedicated to genetic or cells therapy.

This field of research consists of a modification of specific sequences present in a cell genome (a prokaryote or an eukaryote cell genome). The introduced modification may result in inactivation of a gene expression, altered gene expression or modified gene expression and also modify gene sequence this is essential for studying genes function(s).

In addition, the same method can be used to correct a gene by restoring the normal phenotype as some therapeutics potential.

This approach also allows a person skilled in the art to generate from genetically modified cell lines (clones) individuals (prokaryote cells, eukaryote cells or organisms made of said cells) presenting a new physiological characteristic of an economic interest (such as prokaryote cells, eukaryote cells, plants or animals producing proteins or other compounds of interest).

Non human genetically engineered mammals (mouse, rat, sheep, etc) or plant models (*Arabidopsis thaliana*) are used for the study of human diseases or for improving plant or animal species.

Furthermore, animal models of human diseases are important to medical researches for studying the efficacy of new treatments before conducting clinical trials on human subjects.

This "genome engineering" method usually requires firstly an identification of a target genomic region in a cell genome, preferably a polynucleotide region encoding for a protein involved in a specific biochemical pathway.

Thereafter, the identified target polynucleotide region of the cell genome (hereafter called 'target polynucleotide region') can be genetically modified by gene targeting techniques that allow a substitution of at least one nucleotide with another nucleotide, a deletion of nucleotide sequences (of several Kb), or an incorporation of new nucleotide sequences into the cell genome.

These gene targeting techniques can be viewed as a form of artificial site directed in vivo mutagenesis.

These genetic modifications can be definitive (present in all the cells of an individual) or maintained for a specific delay under controlling elements (present in some specific cells of an individual under the control of the scientists performing the experiments) (M. Bunting et al. Genes & Dev. 1999, vol. 13, p. 1524-1526) and are preferably obtained by a recombination event that allows integration of exogenous nucleotide sequences in this 'target polynucleotide region' of the cell genome.

Typically, for this genetic modification an exogenous nucleotide sequence incorporated into a vector (insertion vector or replacement vector, such as a plasmid or a virus) will comprise a nucleotide fragment of interest flanked by two recombination arms.

These recombination arms share common sequence portions of homology with two flanking sequences of a target site of the target polynucleotide region.

Therefore, an homologous recombination event between the two recombination arm sequences and the flanking sequence of the target site will result in the insertion of the exogenous nucleotide sequence into the target site.

Advantageously, the target site of the target polynucleotide region could correspond to a gene which following the recombination event is therefore replaced by the exogenous nucleotide sequence.

The vector according to the invention or the exogenous nucleotide sequence may further comprise markers of positive or negative selection. Based upon the activity of these markers (markers of positive selection) or based upon the deletion of these markers (markers of negative selection) into specific cell lines (clones), it is possible to identify and select cells having integrated these exogenous nucleotide sequences. Positive selectable markers are preferably detectable by addition of antibiotics to cell cultures or are detected by light emission (US patent application 2004/0214222).

However, among these selected transformed cell lines, only a minority of the cells have integrated correctly the exogenous nucleotide sequences into the target polynucleotide region of the cell genome.

It is also necessary to perform additional screening step(s) upon each of these cell lines (these cells have a common ancestor and represent thus a clone) in order to identify and select which cell lines (which clone) have integrated the exogenous nucleotide sequences correctly (e.g. in the target polynucleotide region of the cell genome, in the correct orientation and with the number of required copies).

After this screening step(s), the clones of interest are recovered for a possible regeneration of complete individual(s) (poly-cellular eukaryotic organisms, such as an animal or a plant) from this recovered genetically modified cell line.

These screening steps are extremely long, costly, and require qualified people for maintaining all these cell lines alive (usually by a cryo-conservation of these cell lines).

Furthermore, a cryo-conservation reduces heavily the recovery cell lines and therefore affects the quality of the experience.

However, all the methods of the state of the art which are extremely long and complicated, cannot identify if the selected transformed cell lines comprise the number of required copies of foreign nucleotide sequences following multiple integration.

Indeed, this type of multiple integration with a high number of copies may present several drawbacks, especially in the field of plant genetics.

Homologous recombination in mammalian cells is a very rare occurrence. In embryonic totipotent mouse cells (ES cell) said occurrence is generally about 1% or lower depending on different factors.

The frequency of homologous recombination depends on the cell characteristics, the sequence homology degree between recombination arms and target sequences and the length of these recombination arms.

Gene targeting by homologous recombination has been achieved in some somatic mammalian cells, where the rate is usually lower than 1/1000. In plant cells, the homologous recombination degree is also very low.

Therefore, in order to improve the frequency of homologous recombination in these cells, it is usually necessary to either select some specific somatic cells of this animal or plant, which can be submitted to a higher percentage of homologous recombination or to improve the characteristics of a vector which comprises longer recombination arms.

However, the development of such vector is rather complicated and expensive.

SUMMARY OF THE INVENTION

In some embodiments, the invention provides a new process and means for (high trough-put) screening detection of genetic modifications in genome engineering, preferably, following recombination.

In some embodiments, the invention provides such a method which does not present the drawbacks of the state of the art.

In some embodiments, the invention provides such a method and means which apply for a genome engineering of different prokaryote or eukaryote cells or organisms, including animals and plant cells or organisms.

In some embodiments, the invention provides such a method and means that simplify the identification and selection steps that are applied upon each transformed cell lines, in order to identify which cell lines have correctly integrated exogenous nucleotide sequences.

In particular, in some embodiments, the present method and means according to the invention aims to reduce the time and costs for said identification and selection steps and aims to provide a method and means which allow an automation, preferably a high-through put screening automation of this identification and selection steps.

This automation is particularly important for improving homologous recombination, transformation method which presents a rate which is usually low. This automation will therefore reduce the time and the efforts for selecting cells wherein a correct homologous recombination has been obtained.

In some embodiments, the invention provides such a method and means which allow to identify and select cell lines which comprise the correct number of the required copies of this exogenous nucleotide sequence after recombination.

Finally, in some embodiments, the present invention provides a method for the monitoring of these genetic modifications through generations.

In some embodiments, the invention provides a method for a (high through-put) screening detection of genetic modifications in a genome which comprises the steps of:

selecting as a target nucleotide site of a cell genome, a target sequence portion of the cell genome to be genetically modified;

providing a vector comprising an exogenous nucleotide sequence flanked by two recombination arms having different sequences corresponding to two target sequences flanking the target sequence portion of the cell genome; wherein, at least one of the two recombination arms comprises in its sequence, a modified nucleotide, said modified nucleotide being different from a corresponding nucleotide existing in the corresponding target nucleotide sequence of the cell genome;

transforming cells with the vector and obtaining an homologous recombination between the arms of the vector and the corresponding target nucleotide sequences of the genome of the cell;

selecting and cloning the transformed cells into clones (cell lines);

extracting the genomic DNA of the said clones;

amplifying with primers the recombination arm sequence comprising the modified nucleotide from the extracted DNA (and its complementary strand, also hereafter defined as a homologous genomic sequence) into amplified sequences;

detecting and selecting by a quantitative sequencing of these amplified sequences, clones wherein only a target sequence portion of the cell genome has been replaced by the exogenous nucleotide sequence;

detecting cells in which the recombination event took place with one or more additional non specific integration(s); and recovering the said detected and selected clones and this in a minimum of time to limit or eliminated cryopreservation of clones.

In some embodiments, the method further comprises recovering a non human pluricellular organism from the said recovered clones and, In some embodiments, the method further comprises selecting (by cross-breeding) a non human pluri-cellular organism presenting homozygously (on the two alleles of its cell genome), the exogenous nucleotide sequence.

An alternative to this method will consist in the step of providing a vector, which consists of an exogenous nucleotide sequence flanked by two recombination Lox sites, which allow an homologous combination with a target sequence portion of the cell genome to be genetically modified, said vector comprising also two recombination arms having different sequences corresponding to two target sequences flanking the target sequence portion of the cell genome. Furthermore, said exogenous nucleotide sequence could comprise at least one modified nucleotide, said modified nucleotide being different from the corresponding nucleotide existing in the corresponding target nucleotide sequence of the cell genome. The method may comprise the step of amplifying with primers a portion of the exogenous nucleotide sequence comprising said modified nucleotide and detecting and selecting by a quantitative sequencing of this amplified sequence clones wherein only a target sequence portion of the cell genome has been replaced by the exogenous nucleotide sequence, this exogenous nucleotide sequence comprising the modified nucleotide.

In the method according to the invention, the quantitative sequencing allows a signal detection proportional to the number of bases present in the amplified sequences.

Preferably, the recovered detected and selected clones are clones wherein only the target sequence portion of the cell genome has been replaced by the exogenous nucleotide sequence and from which the quantitative sequence of the amplified sequence results in a quantification of a signal, corresponding to the presence of a ½ modified nucleotide and ½ unmodified nucleotide.

In the method according to the invention, the cell is an embryonic totipotent pluri-cellular cell or a somatic cell. Preferably, the vector according to the invention is a knock-out vector or an integration vector and the regenerated pluri-cellular organism is a non human vertebrate, preferably, a non human mammal, such as a mouse or a rat.

In another preferred embodiment of the present invention, the regenerated non human pluri-cellular organism is a plant.

Another aspect of the present invention is related to a system (kit or device) for the targeting of an exogenous nucleotide sequence into a cell genome, which comprises (i) the vector above described (comprising an exogenous nucleotide sequence flanked by two recombination arms having sequences that correspond to two target nucleotide sequences flanking a target sequence portion of a cell genome, wherein at least one of the two recombination arms comprises in its sequence a modified nucleotide, said modified nucleotide being different from the corresponding nucleotide existing in the corresponding target nucleotide sequence of the cell genome), (ii) primers able to amplify the said recombination arm sequences comprising the modified nucleotide and its complementary strand, and (iii) primers for a quantitative sequencing of the sequence of the said recombination arm and its complementary strand. In some embodiments, the kit further comprises (iv) cells comprising in their genomes the said target sequence portion to be modified.

The present invention will be described in details in reference to the enclosed figures as a non-limited illustration of the scope of the present invention.

Definitions

A "vector" is a double-stranded extra chromosomal nucleic acid construct that includes cloning and expression vehicles, such as viral or plasmid vector. A vector is capable of transferring exogenous nucleotide sequences to target cell, typically a vector construct expression, insertion vector and replacement vector means any nucleic acid construct that can transfer nucleotide sequences to a target cell genome. The vector could be a circular or a linear vector.

A "target site" is a pre-determined location within a cell genome into which integration of exogenous nucleotide sequence is desired. Said target site could correspond to a contiguous target sequence portion which can be replaced by an exogenous nucleotide sequence.

A "target site" is defined by flanking target sequences that allow a recombination with the recombination arms of the vector according to the invention.

"Homologous recombination" or "homologous recombination event" means the integration of an integration element (vector) that includes an exogenous nucleotide sequence. This exogenous nucleotide sequence comprises at least a nucleotide fragment of interest flanked by two recombination arms that provide for homologous recombination into a target genome (preferably, in a target polynucleotide sequence portion of a cell genome) by a mechanism that is facilitated by there being a sufficiently high level of sequence identity (e.g. at least 95%, preferably at least 99% (including 100% sequence identity)) between each of the recombination arms of the exogenous nucleotide sequence and the corresponding flanking sequences of the target site of integration of the target genome. Homologous recombination results in the insertion into the target genomic site of the integration element.

"Gene targeting" describes the site specific integration of an exogenous nucleotide sequence into a specific target site of a target genome by recombination.

By "nucleotide fragment of interest", it is meant any nucleotide acid fragment adapted for insertion into a cell genome. Suitable examples of nucleotide fragments of interest include promoter elements, therapeutic genes, marker genes, control regions, trait-producing fragments, nucleic acid elements to accomplish gene disruption, or a mixture thereof. A nucleotide fragment of interest may additionally be an "expression cassette".

An "expression cassette" comprises any nucleic acid construct capable of directing the expression of a gene/coding sequence of interest. A nucleotide fragment of interest may also be a "disrupting" nucleic acid where the disrupting nucleic acid, once integrated into a target site, will disrupt the expression of a gene in the vicinity of the target site (may alter the coding sequence of the gene, may interfere with the transcription, splicing or translation of the gene or may itself express a disruptive (e.g. antisense nucleic acid).

Methods of transforming cells are well known in the art. By "transformed" it is meant an alteration in a cell resulting from the uptake of exogenous nucleotide sequence, usually DNA. Suitable methods include viral infection, transfection, conjugation, protoplast fusion, electroporation, particle gun technology, calcium phosphate precipitation, direct microinjection or a mixture thereof. The choice of the method is generally dependent on the type of the cell being transformed and the circumstances under which the transformation is taking place (in vitro, ex vivo or in vivo). (see Ausubel et al, Short Protocols in Molecular Biology, $4^{th}$ ed., Wiley & Sons, 1999).

The terms "nucleotide molecule", "nucleotide sequence", "nucleic acid molecule" and "polynucleotide" are used interchangeably and refer to a polymeric form of nucleotides of any length, either DNA, RNA or analogs thereof. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers (linear or circular).

A "coding sequence" or a sequence which "encodes" a selected polypeptide, is a nucleotide molecule which is transcribed (in the case of DNA) and translated (in the case of mRNA) into a polypeptide, for example, in vivo when placed under the control of appropriate regulatory sequences (or "control elements").

By "nucleic acid construct" it is meant a nucleic acid sequence that has been constructed to comprise one or more functional units not found together in nature. Examples include circular, linear, double-stranded, extra-chromosomal DNA molecules (plasmids), cosmids (plasmids containing COS sequences from lambda phage), viral genomes comprising non-native nucleic acid sequences and the like.

Techniques for determining nucleic acid and amino acid "sequence identity" are also known in the art. Appropriate alignment of nucleotide sequences can be obtained by homology algorithms well described in the scientific literature.

An "endonuclease" describes any molecule capable of severing, internally, the covalent linkage of a DNA chain of nucleotides resulting in a double stranded break at different sequences of a double stranded nucleic sequence substrate where the particular sequence is termed an "endonuclease site". An endonuclease may be a DNAse (a restriction endonuclease) or a recombinase (a transposase, resolvase, integrase, invertase).

A "recombinase system" includes for instance the Cre-LoxP recombination system of a bacteriophage P1. The natural function of Cre (causes recombination) is to obtain a recombination between two LoxP sequences that are in the same orientation leading to excision of the intervening sequence between the two LoxP sites. The subsequent provision of a gene encoding the Cre product can result in an artificial generated site directed recombination event in specific tissues or cells.

DETAILED DESCRIPTION OF THE PREFERRED EMBODIMENT

The present invention aims to improve the efficacy of a homologous recombination method by providing a vector (1) that comprises an exogenous nucleotide sequence (2) flanked by two recombination arms (3,4). These two recombination arms (3,4) comprise two different nucleotide sequences corresponding (this means that they preferably are essentially identical and present a high sequence identity of at least 95%, 98%, 99%, preferably almost 100% sequence identity) with two target nucleotide sequences (5,6) flanking a target site in the target genome of a cell to be transformed by the vector of the invention.

Preferably, said target site is a target sequence portion (8) of the cell genome (9) to be transformed by the vector (1) of the invention.

However, in the method of the invention, at least one of the two recombination arms (3,4) comprises in its sequence a modified nucleotide (7) different from the corresponding unmodified nucleotide (14) present in the corresponding nucleotide sequence (5).

Therefore, a recombination event in the cell (between the two arms (3,4) and their corresponding target sequences (5,6)) will result into the replacement of at least these two sequences (5,6) by their two corresponding recombination arms (3,4) and with the introduction of the exogenous sequence (2) flanked by these two recombination arms (3,4) into the genome (9) of the cell. This recombination event will also result in the deletion of the target sequence portion (8) replaced by the exogenous sequence (2).

This means that the genome (9) of the cell will comprise at the target site, an insert comprising at least an exogenous nucleotide sequence (2) flanked by the two recombination arms (3,4) with one arm (3) comprising the "modified" nucleotide (7) different from the corresponding nucleotide (14) that was initially present in the deleted corresponding (unmodified) target nucleotide sequence (5) (change of one base (14)) (ATC or G) by another base (7) (CGA or T). The genome (9) of the cell can comprise other elements of the insert (one or more selection markers (11) or other elements (regulatory sequences) of the transfection vector (1).

Preferably, the "modified" nucleotide (7) is present spatially close to the exogenous sequence (2) and can be used as a specific marker of the insert in the transformed cell.

The present invention allows a further identification and selection step applied with said modified nucleotide sequence (7) as a marker.

Preferably, this method is more convenient than the method of the state of the art which requires a detailed analysis (labeling, southern blotting, amplification, sequencing, . . . ) of the exogenous sequence (2), which are rather complicated and time consuming. These conventional approaches need to be adapted before their use in screening method (test of the probe, design an validation of PCR primers in the context of a non recombinant genome). The proposed method can be easily (primer design being standard) set up on the wild type genome and be used on the recombinants candidates.

Figure 1:
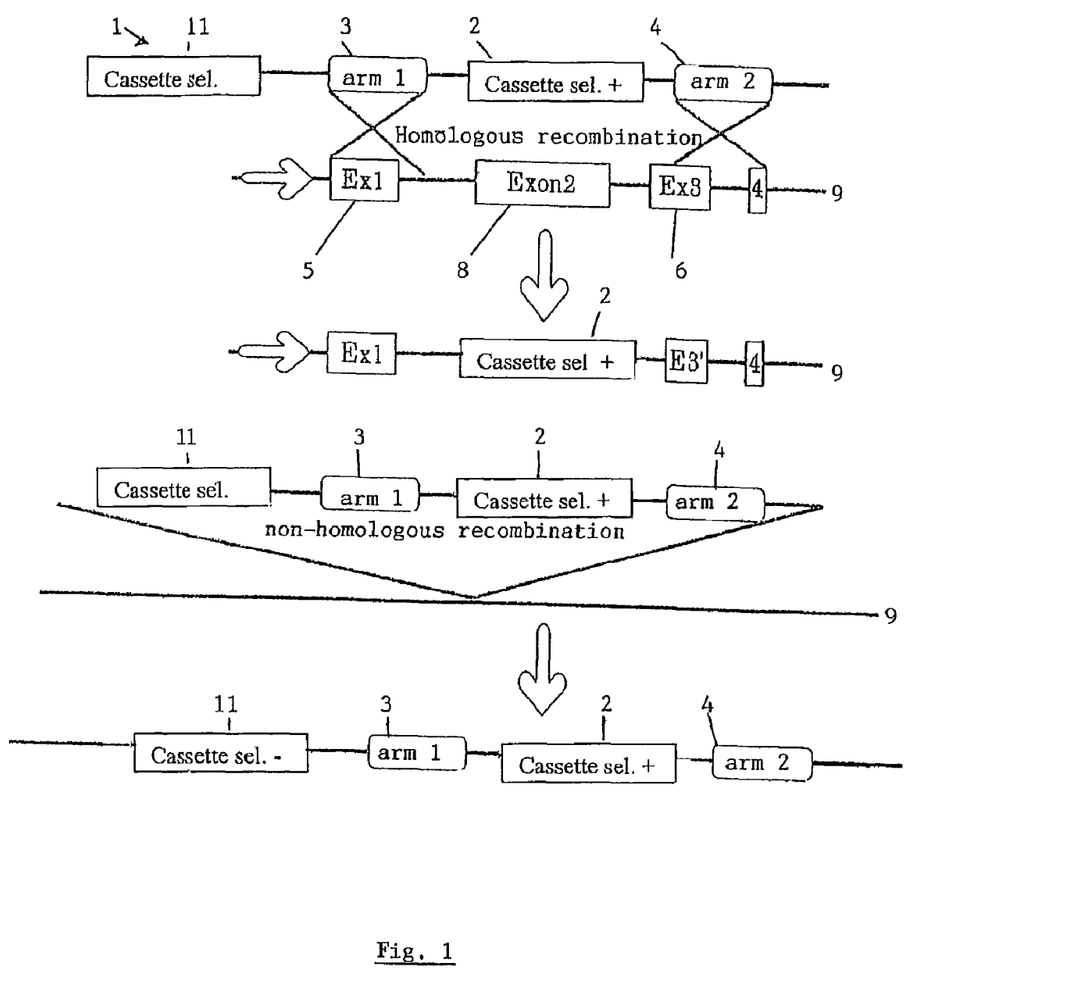
FIG. 1 to FIG. 4 represents the different steps of the high through-put screening steps according to the invention.

In the method according to the invention, a selection of the cell lines (clones) can be obtained by a positive or negative selection with positive or negative selection markers (11), which, in some embodiments, may be present in the vector (1) and the resulted insert according to the invention. These markers (11) are used for the identification of the inserts obtained by homologous recombination or not (FIG. 1).

However, this selection step could not be used for selecting only the cell lines (clones) having integrated correctly foreign DNA sequences.

Therefore, in order to identify which cell lines (clones) have been submitted to an homologous recombination step according to the desired strategy (specific and correct integration of the foreign DNA sequence at the target site of insertion in the correct orientation and with the number of desired copies), the method according to the invention is also characterized by an additional step which comprises an extraction of a genomic DNA from the transformed cell lines (clones).

Figure 2:
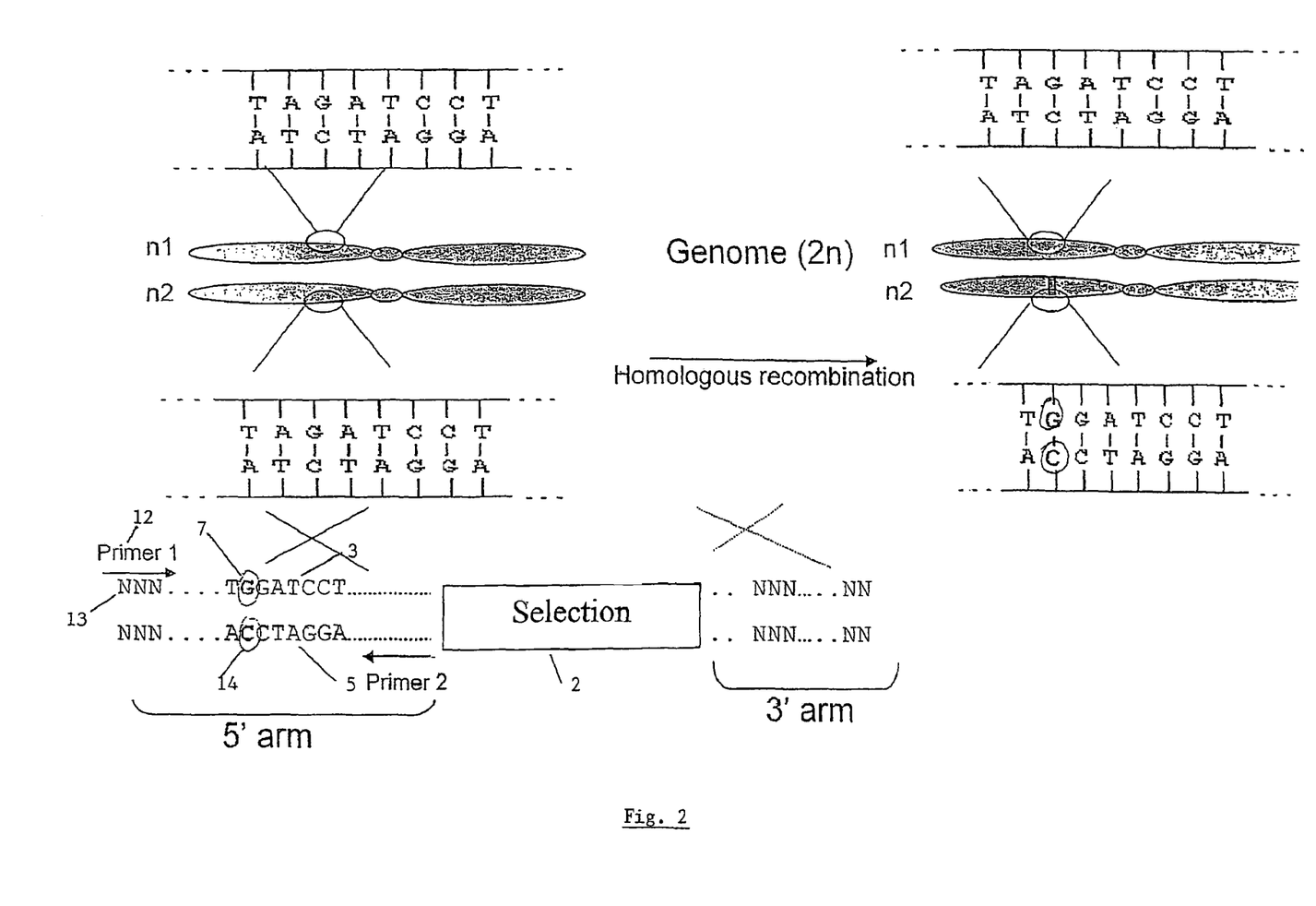
Figure 3:
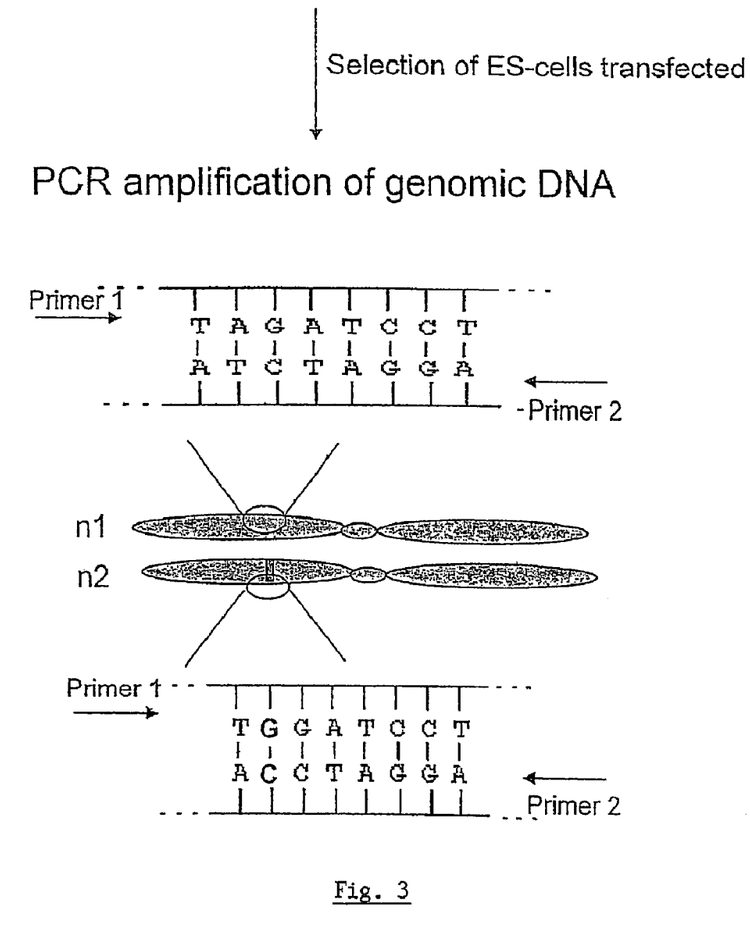

This genomic DNA is thereafter submitted to a genetic amplification with primers (12) that can (only) hybridize with specific nucleotide portions (13) located close to, or in the recombination arm (3) comprising the modified nucleotide (7) or its complementary strand (10) (see FIG. 2). These primers are used for an amplification of this arm (3) or a portion of this arm (3) comprising the modified nucleotide (7) and the complementary strand (10).(see FIGS. 2 to 4) This genetic amplification is preferably a PCR amplification. The genetic amplification is followed by a quantitative sequencing, preferably a pyro-sequencing (see FIG. 3) providing signal detection proportional to the number of bases.

Four different recombination events can be obtained and characterized:

1. no homologous recombination and integration of the exogenous sequence (2) was obtained with the transformation vector (no allele modified);
2. a random integration of the exogenous sequence (2) was obtained, but none at the target site, with the target sequence portion (8) of the cell genome (9) (one allele modified);
3. a correct integration of the exogenous sequence (2) was obtained at the target site with the target sequence portion (8) of the cell genome (9)(one allele modified correctly);
4. a correct integration of the exogenous sequence (2) at the target site with the target sequence portion (8) of the cell genome (9) was obtained, but one or more additional random integration(s) of the exogenous sequence (2) at other sites with other portions of the cell genome (9) was also obtained (one allele modified).

By the quantitative sequencing analysis method according to the invention and by the specific detection of the modified nucleotide (7) present in the recombination arm (3), it is possible to characterize and qualify which type of recombination event was obtained in each cell line (clone). Such quantitative analysis can be put into evidence for the four above mentioned recombination events and therefore, one may select the cell lines (clones) having the desired recombination events.

In the absence of a recombination event (event n° 1), there is no detection of a modified allele and the quantitative sequencing will result in a quantification of the two alleles (½ unmodified nucleotide (14)+½ unmodified nucleotide (14)) that are not genetically modified.

In the case of multiple or unique random integration of the exogenous nucleotide sequence (2) (event n° 2), there is a detection of a modified allele, but the quantitative sequencing will result in a detection of n (number of random integration×½ modified nucleotide (7) present in the modified allele)+½ unmodified nucleotide present in the second unmodified allele+½ unmodified nucleotide (14).

If a correct integration of the exogenous nucleotide sequence (2) was obtained (event n° 3) at the target site with the target sequence portion (8) of the cell genome (9), the quantitative sequencing will always result in a quantification of ½ modified nucleotide (7) (modified allele) and ½ unmodified nucleotide (14) (unmodified allele). This means that one allele is not modified while the other allele is modified by a correct integration of the exogenous sequence (2) in the target site. This means also that the target sequence portion (8) of the cell genome has been deleted and replaced by the exogenous nucleotide sequence (2).

If a correct integration of the exogenous nucleotide sequence (2) in the target site was obtained (as in event n° 3), in addition to one or more random integration(s) (event n° 4), the quantitative sequencing will result in a quantification of n (number of random integration)×½ modified nucleotide (7) (modified allele)+½ unmodified nucleotide (14) (unmodified allele)+½ modified nucleotide (7) (modified allele).

Therefore, this quantitative sequencing could also be used for the identification of cells which have been submitted to the requested homologous recombination event, but have been contaminated by another cell clone during the isolation process (submitted to the requested recombination event or not).

In this last case, the quantification of the unmodified nucleotide (14) is higher than ½.

The method according to the invention may comprise finally a step of selecting and recovering of the correctly modified cell lines (clones).

Furthermore, the integration of the modified nucleotide into the genome of the cell close to the target site could be used as a marker (transgenic marker) to follow different and multiple genetic modifications through generations and identify if these successive generations maintain the presence of these various and different exogenous sequences and therefore allow a person skilled in the art to select through crossbreeding the organisms or cells presenting (homologous or heterogous) the required genetic modifications.

Preferably, the modified nucleotide (7) introduced into the recombination arm (3) is selected in order to avoid any genetic perturbation into the genome (9) of the transfected cell. Said punctual modification of a nucleotide (7) is a silencing modification (i.e. which will not modify the corresponding amino-acid composition), especially if the homologous recombination is done between a recombination arm (3) and a target sequence (5) which is a coding sequence.

The method according to the invention may be further combined with one or more regeneration steps of tissues or organisms from the genetically modified cell lines (clones). These steps are well known by the person skilled in the art and described in the scientific literature (K. R. Thomas et al. Cell, 1987, vol. 51(3),p. 503-512); Galli—Thaliodoros, C. A. et al. J. Immuno. Meth. 1995, vol. 181, p. 1-15; Muller U. Mechanisms of Development, 1999, vol. 82, p. 3-21; Terrihiko Wakayama et al. PNAS, 1999, vol. 96, p. 14984-14989); A. Pfeifer et al. PNAS, 2002, vol. 99, p. 2140-2145) and proposed by several companies (lexicon-genetics, genoway and deltagen).

Preferably, this genetically modified cell line clone is a stem cell line of an eukaryote organism, preferably non-human totipotent embryonic stem cells (such as mouse ES cells) which could be used for obtaining easily a regeneration of a non-human mammal (preferably a rodent, such us a mouse or a rat) from this cell line.

The method according to the invention may also comprise a step of gene targeting using the Cre-LoxP recombination system to inactivate a gene in a desired cell type. Such tissue restructured limitation is well known by the person skilled in the art and described in the scientific literature (Zhi-Wey Li et al. PNAS, 1996, vol. 93, p. 6158-6162).

The method according to the invention can be performed by an automate which comprise means and media for performing these various steps. Some of these means and media are already described in the state of the art or are already included in various devices sold by various companies.

The vector according to the invention is preferably presented in a system (kit or device) for homologous recombining an exogenous nucleotide sequence into a target sequence of the cell genome, with other means and media for performing the method according to the invention.

Preferably, said system (kit or device, preferably an automate) may further comprise primers (12) that can hybridize with specific nucleotide portions (13) located close to or in the recombination arm (3) comprising the modified nucleotide (7). These primers are selected in order to obtain an amplification and possibly a quantification of the presence of the recombination arm (3) sequence or a portion thereof, with the modified nucleotide (7) (or a complementary strand (10) thereof) in the genome (9) of the genetically modified cell.

The other means and media present in the system (screening kit or device) are endonucleases (preferably recombinases) and cells (preferably, embryonic totipotent mammal cells, such as mouse ES cells). Said cells are selected in order to allow by a high transfection rate, the regeneration of a non human pluri-cellular organism from these cells.

The present invention will be described in details in the following example presented as a non-limiting illustration of the embodiments of the present invention.

EXAMPLES

Identification of Homologous Recombination by Identification of a Mutated Base in Genomic DNA by Pyrosequencing Selection of the Genomic DNA and Primers:

The following genomic DNA has been selected: SEQ ID NO 1 (top strand) and SEQ ID NO: 2 (bottom strand).

ACTGAGGAAGACCTTGAGGAAGCTGGGGTGCAGGATCCTGCTCACAAGCGCCTTCTTC<u>T</u>
TGACTCCTTCTGGAACTCCTTCGACCCCACGTCCTAGGACGAGTGTTCGCGGAAGAAGA
    Fw primer
<u>GGACACCTTGCAGCTCAGC</u>AAATGATTGCAGAGGTGCTGCCCAGCTGCAAAAGCGGAGC
CCTGTGGAACGTCGAGTCGTTTACTAACGTCTCCACGACGGGTCGACGTTTTCGCCTCG                                                                             Seq. primer
TGGATGGGCACGTGCAACCAGGGGTTGAAAGTTCGGAGCGGTGTGGCCGTGCATCTCTA

ACCTACCCGTGCACGTTGGTCCCCAACTTTCAAGCCTCGCCACACCGGCACGTAGAGAT

T
GTTATTGGGGATCAGAGTTCCCTACTGCCCAGTTGTTTGGGACATTCTAGTTAAAACAT
CAATAACCCCTAGTCTCAAGGGATGACGGGTCAACAAACCCTGTAAGATCAATTTTGTA
A

CGTGCTCCCCAGCTCCCCACCTAGCTTTTAGGCCCGGGGGGGGGGGGTGCGCAGGGGG
GCACGAGGGGTCGAGGGGTGGATCGAAAATCCGGGCCCCCCCCCCCCACGCGTCCCCC
AGGTTAGTAGCCTGTGGTGATTGTGAAGATCGGTGGTTACGCTGGTGCAGACACCTCCT
TCCAATCATCGGACACCACTAA<u>CACTTCTAGCCACCAATGCG</u>ACCACGTCTGTGGAGGA
                             Rev. primer - biotin Forward (Fw) and reverse (Rev) primers used in the PCR are underlined.
Sequencing primer used in the pyrosequencing is bordered; this primer is labeled with biotin in 5'.
Mutated base are represented in bold and underlined character, these bases are introduced into, the molecule (targeting vector) introduced in the cell in which the sequence will be targeted.
The sequence analyzed by pyrosequencing (see the results) is bordered.

Figure 5:
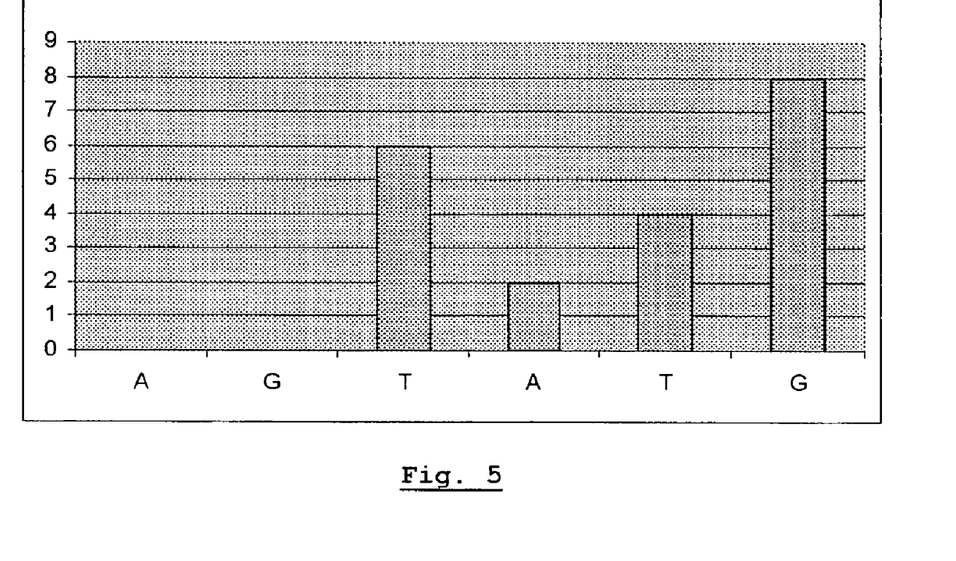
FIG. 5 to FIG. 8 represents different possible results of a quantitative sequencing obtained by the method of the invention.

Results of PCR Following the Recombination
    Four different recombination events can be obtained:

```
1. Non recombination:      Allele 1   . . . TTTAT-        (SEQ ID NO 8)
                                            TGGGG . . .
   (FIG. 5)                            AAATAACCCC . . .   (SEQ ID NO 9)
                           Allele 2   . . . TTTAT-        (SEQ ID NO 8)
                                            TGGGG . . .
                                      AAATAACCCC . . .   (SEQ ID NO 9)

Figure 6:
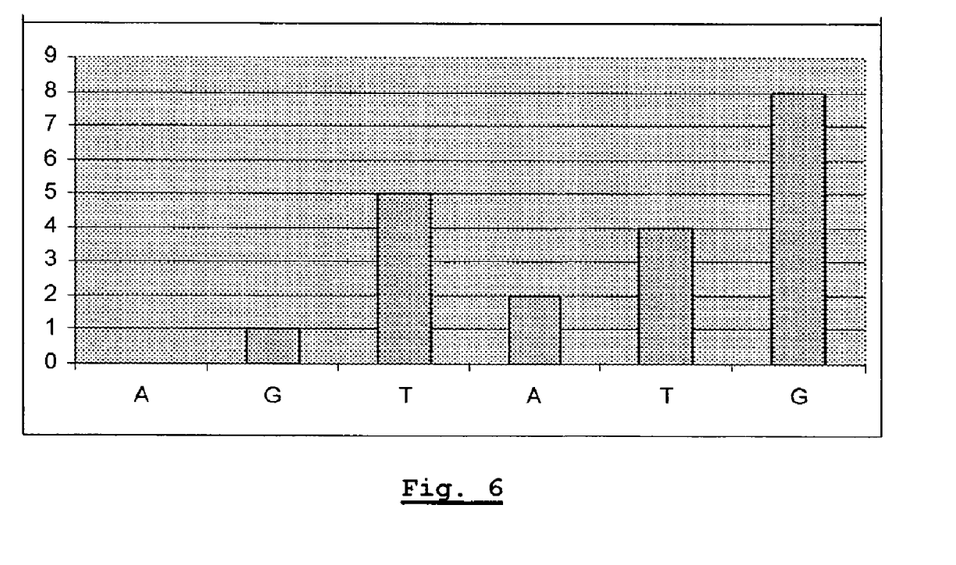

2. Homologous recombination:Allele 1  TTTATTGGGG . . .    (SEQ ID NO 8)
   (FIG. 6)                            AAATAACCCC . . .   (SEQ ID NO 9)
                           Allele 2*  . . . GTTAT-        (SEQ ID NO 10)
                                            TGGGG . . .
                                      CAATAACCCC . . .   (SEQ ID NO 11)
* Allele 2 is targeted and contains the mutation.

Figure 7:
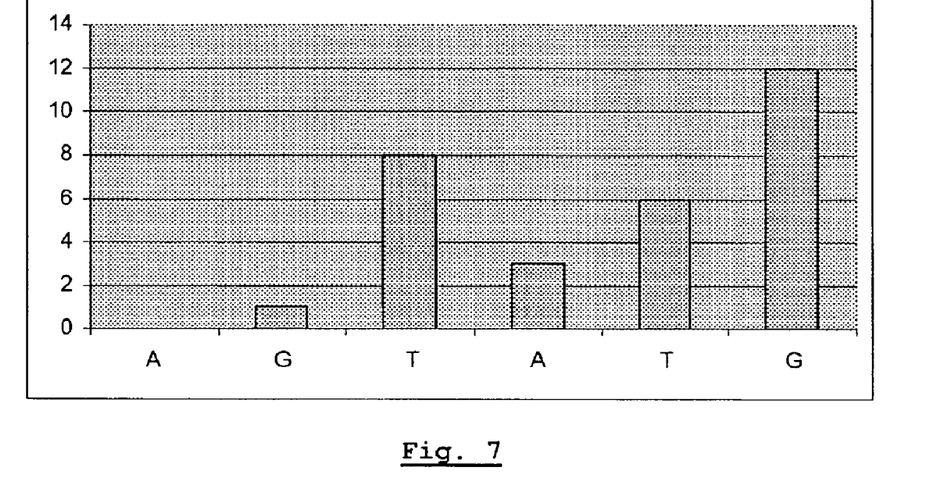

3.   Random integration:   Allele 1   . . . TTTAT-        (SEQ ID NO 8)
                                            TGGGG . . .
   (FIG. 7)                           . . . AAATAAC-      (SEQ ID NO 9)
                                            CCC . . .
                           Allele2    . . . TTTAT-        (SEQ ID NO 8)
                                            TGGGG . . .
                                      . . . AAATAAC-      (SEQ ID NO 9)
                                            CCC . . .
                           + 1R X*    . . . GTTAT-        (SEQ ID NO 12)
                                            TGGGG . . .
                                      . . . CAATAAC-      (SEQ ID NO 13)
                                            CCG . . .
In this case, the chart shows unique random integration.
* integration in a non homologous site (could be multiple)

Figure 8:
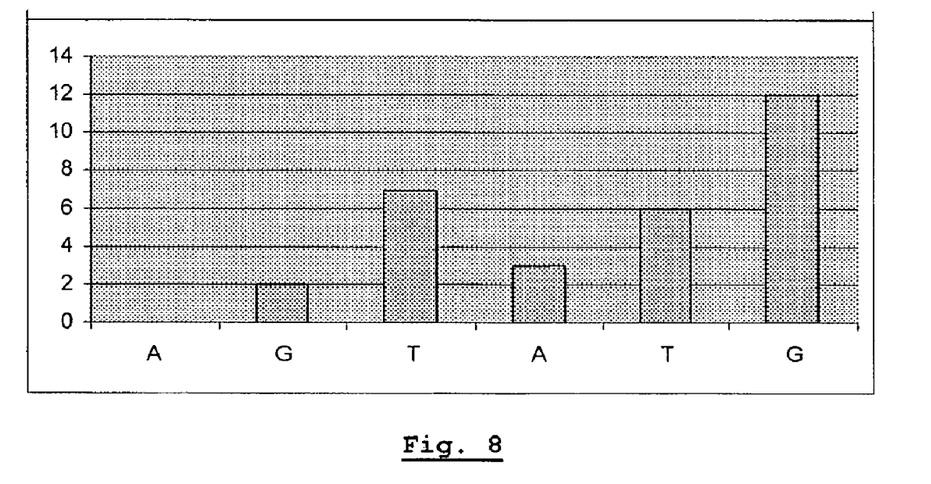

4. Homologous recombination Allele 1  . . . TTTAT-        (SEQ ID NO 8)
                                            TGGGG . . .
   with random integration:           . . . AAATAAC-      (SEQ ID NO 9)
                                            CCC . . .
   (FIG. 8)
                           Allele2*   . . . GTTAT-        (SEQ ID NO 10)
                                            TGGGG . . .
                                      . . . CAATAAC-      (SEQ ID NO 11)
                                            CCC . . .
                           + 1R X**   GTTATTGGGG . . .    (SEQ ID NO 12)
                                      . . . CAATAAC-      (SEQ ID NO 13)
                                            CCG . . .
In this case, the chart (see below) shows unique random
integration.
* integration at the homologous site
**integration in a non homologous site (could be multiple)
```

The enclosed FIGS. 5 to 8 present the results of pyrosequencing following the above-identified 4 cases. The biotin-labeled strand is pyrosequenced with seq primer.

What is claimed is:

1. A method for a screening detection of genetic modifications in a genome comprising:
    selecting as a target nucleotide site of a cell genome, a target sequence portion of the cell genome to be genetically modified;
    providing a vector comprising an exogenous nucleotide sequence flanked by two recombination arms corresponding to two target sequences flanking the target sequence portion of the cell genome; wherein, at least one of the two recombination arms comprises in its sequence, a modified nucleotide, said modified nucleotide being different from a corresponding nucleotide existing in the corresponding target nucleotide sequence of the cell genome;
    transforming cells by the vector and obtaining transformed cells wherein an homologous recombination between the arms of the vector and the corresponding target nucleotide sequences of the genome of the cell occurs;
    selecting and cloning the transformed cells into clones, wherein said clones are not human beings;
    extracting the genomic DNA of the clones;
    amplifying with primers the recombination arm sequence comprising the modified nucleotide or its complementary strand sequence, into amplified sequences;
    detecting and selecting by a quantitative sequencing of the amplified sequences, clones wherein only the target sequence portion of the cell genome has been replaced by the exogenous nucleotide sequence; and
    recovering the detected and selected clones.

2. A method according to claim 1, wherein the quantitative sequencing allows signal detection proportional to the number of bases present in the amplified sequences.

3. The method according to claim 2, wherein the recovered clones are clones from which the quantitative sequencing of the amplified sequences, results in a quantification of a signal corresponding to the presence of ½modified nucleotide present in a modified allele and ½unmodified nucleotide present in an unmodified allele.

4. The method according to claim 1, wherein the cell is an embryonic totipotent cell obtained from a pluri-cellular organism.

5. The method according to claim 1, wherein the vector is a knock-out vector.

6. The method according to claim 1, wherein the vector is an integration vector.

7. The method according to claim 1, wherein the cell is a non-human vertebrate cell.

8. The method according to claim 7, wherein the non-human vertebrate is a mouse or a rat.

9. The method of claim 1 further comprising recovering a non human pluri-cellular organism from the recovered clones.

10. The method according to claim 9, wherein the pluri-cellular organism is a plant.

11. A kit for homologously recombining an exogenous nucleotide sequence into a target cell genome according to claim 1 comprising:
    a vector comprising an exogenous nucleotide sequence flanked by two recombination arms having sequences that correspond to two target nucleotide sequences flanking a target sequence portion of a cell genome, wherein at least one of the two recombination arms comprises in its sequence a modified nucleotide, the modified nucleotide being different from the corresponding nucleotide existing in the corresponding target nucleotide sequence of the cell genome;
    primers for amplifying the recombination arm sequence comprising the modified nucleotide and its corresponding strand; and
    a primer for a quantitative sequencing of the recombination arm or its corresponding strand.

12. The kit of claim 11 further comprising cells comprising in their genome, a target sequence portion to be modified.

* * * * *

SEQUENCE LISTING

<160> NUMBER OF SEQ ID NOS: 17

<210> SEQ ID NO 1
<211> LENGTH: 354
<212> TYPE: DNA
<213> ORGANISM: mouse
<220> FEATURE:
<221> NAME/KEY: misc_feature
<223> OTHER INFORMATION: Mouse genomic DNA

<400> SEQUENCE: 1

```
actgaggaag accttgagga agctggggtg caggatcctg ctcacaagcg ccttcttctg    60
gacaccttgc agctcagcaa atgattgcag aggtgctgcc cagctgcaaa agcggagctg   120
gatgggcacg tgcaaccagg ggttgaaagt tcggagcggt gtggccgtgc atctctattt   180
attggggatc agagttccct actgcccagt tgtttgggac attctagtta aaacatcgtg   240
ctccccagct ccccacctag cttttaggcc cgggggggggg ggggtgcgca ggggaggtt   300 agtagcctgt ggtgattgtg aagatcggtg gttacgctgg tgcagacacc tcct         354
```

<210> SEQ ID NO 2
<211> LENGTH: 354
<212> TYPE: DNA
<213> ORGANISM: mouse
<220> FEATURE:
<221> NAME/KEY: misc_feature
<223> OTHER INFORMATION: Mouse genomic DNA (opposite strand of Sequence
      ID No: 1)

<400> SEQUENCE: 2

```
aggaggtgtc tgcaccagcg taaccaccga tcttcacaat caccacaggc tactaacctc    60
cccctgcgca cccccccccc cccgggccta aaagctaggt ggggagctgg ggagcacgat   120
gttttaacta gaatgtccca aacaactggg cagtagggaa ctctgatccc caataaatag   180
agatgcacgg ccacaccgct ccgaactttc aaccctggt tgcacgtgcc catccagctc   240
cgcttttgca gctgggcagc acctctgcaa tcatttgctg agctgcaagg tgtccagaag   300
aaggcgcttg tgagcaggat cctgcacccc agcttcctca aggtcttcct cagt         354
```

<210> SEQ ID NO 3
<211> LENGTH: 354
<212> TYPE: DNA
<213> ORGANISM: Artificial Sequence
<220> FEATURE:
<223> OTHER INFORMATION: Genomic mouse DNA with a mutated base
      introduced by homologous recombination

<400> SEQUENCE: 3

```
actgaggaag accttgagga agctggggtg caggatcctg ctcacaagcg ccttcttctg    60
gacaccttgc agctcagcaa atgattgcag aggtgctgcc cagctgcaaa agcggagctg   120
gatgggcacg tgcaaccagg ggttgaaagt tcggagcggt gtggccgtgc atctctagtt   180
attggggatc agagttccct actgcccagt tgtttgggac attctagtta aaacatcgtg   240
ctccccagct ccccacctag cttttaggcc cgggggggggg ggggtgcgca ggggaggtt   300 agtagcctgt ggtgattgtg aagatcggtg gttacgctgg tgcagacacc tcct         354
```

-continued

```
<210> SEQ ID NO 4
<211> LENGTH: 354
<212> TYPE: DNA
<213> ORGANISM: Artificial Sequence
<220> FEATURE:
<223> OTHER INFORMATION: Genomic mouse DNA with a mutated base
      introduced by homologous recombination (opposite strand of
      Sequence ID No: 3)

<400> SEQUENCE: 4
aggaggtgtc tgcaccagcg taaccaccga tcttcacaat caccacaggc tactaacctc    60
cccctgcgca ccccccccc cccgggccta aaagctaggt ggggagctgg ggagcacgat    120
gttttaacta gaatgtccca aacaactggg cagtagggaa ctctgatccc caataactag   180
agatgcacgg ccacaccgct ccgaactttc aaccccctggt tgcacgtgcc catccagctc   240
cgcttttgca gctgggcagc acctctgcaa tcatttgctg agctgcaagg tgtccagaag   300
aaggcgcttg tgagcaggat cctgcacccc agcttcctca aggtcttcct cagt          354

<210> SEQ ID NO 5
<211> LENGTH: 20
<212> TYPE: DNA
<213> ORGANISM: Artificial Sequence
<220> FEATURE:
<223> OTHER INFORMATION: Forward primer

<400> SEQUENCE: 5
tggacacctt gcagctcagc                                                20

<210> SEQ ID NO 6
<211> LENGTH: 20
<212> TYPE: DNA
<213> ORGANISM: Artificial Sequence
<220> FEATURE:
<223> OTHER INFORMATION: Biotinylated reverse primer

<400> SEQUENCE: 6
gcgtaaccac cgatcttcac                                                20

<210> SEQ ID NO 7
<211> LENGTH: 15
<212> TYPE: DNA
<213> ORGANISM: Artificial Sequence
<220> FEATURE:
<223> OTHER INFORMATION: Sequencing Primer

<400> SEQUENCE: 7
ggccgtgcat ctcta                                                     15

<210> SEQ ID NO 8
<211> LENGTH: 10
<212> TYPE: DNA
<213> ORGANISM: mouse
<220> FEATURE:
<221> NAME/KEY: misc_feature
<223> OTHER INFORMATION: PCR product in case of non recombination

<400> SEQUENCE: 8
tttattgggg                                                           10

<210> SEQ ID NO 9
<211> LENGTH: 10
<212> TYPE: DNA
<213> ORGANISM: mouse
<220> FEATURE:
<221> NAME/KEY: misc_feature
<223> OTHER INFORMATION: PCR product in case of non recombination
```

-continued (opposite strand of Sequence ID No: 8)

<400> SEQUENCE: 9
ccccaataaa                                                                10

<210> SEQ ID NO 10
<211> LENGTH: 10
<212> TYPE: DNA
<213> ORGANISM: Artificial Sequence
<220> FEATURE:
<223> OTHER INFORMATION: PCR product in case of integration at the
      homologous site

<400> SEQUENCE: 10
gttattgggg                                                                10

<210> SEQ ID NO 11
<211> LENGTH: 10
<212> TYPE: DNA
<213> ORGANISM: Artificial Sequence
<220> FEATURE:
<223> OTHER INFORMATION: PCR product in case of integration at the
      homologous site (opposite strand of Sequence ID No: 10)

<400> SEQUENCE: 11
ccccaataac                                                                10

<210> SEQ ID NO 12
<211> LENGTH: 10
<212> TYPE: DNA
<213> ORGANISM: Artificial Sequence
<220> FEATURE:
<223> OTHER INFORMATION: PCR product in case of random integration

<400> SEQUENCE: 12
gttattgggg                                                                10

<210> SEQ ID NO 13
<211> LENGTH: 10
<212> TYPE: DNA
<213> ORGANISM: Artificial Sequence
<220> FEATURE:
<223> OTHER INFORMATION: PCR product in case of random integration
      (opposite strand of Sequence ID No: 12)

<400> SEQUENCE: 13
gcccaataac                                                                10

Figure 4:
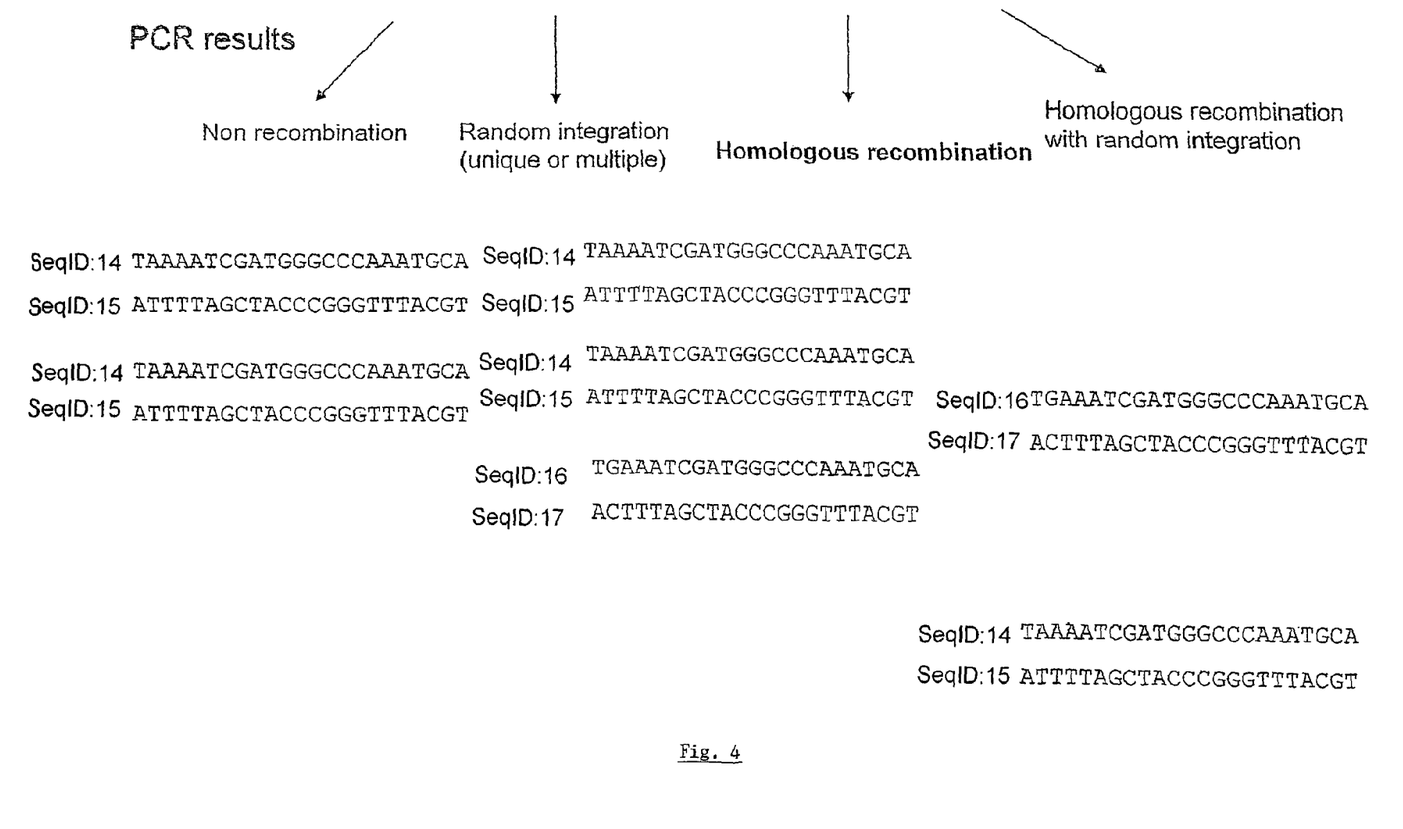

<210> SEQ ID NO 14
<211> LENGTH: 23
<212> TYPE: DNA
<213> ORGANISM: mouse
<220> FEATURE:
<221> NAME/KEY: misc_feature
<223> OTHER INFORMATION: PCR product in case of non recombination
      (Figure 4)

<400> SEQUENCE: 14
taaaatcgat gggcccaaat gca                                                 23

<210> SEQ ID NO 15
<211> LENGTH: 23
<212> TYPE: DNA
<213> ORGANISM: mouse
<220> FEATURE:
<221> NAME/KEY: misc_feature
<223> OTHER INFORMATION: PCR product in case of non recombination
      (opposite strand of Sequence ID No: 14) (Figure 4)

```
<400> SEQUENCE: 15
tgcatttggg cccatcgatt tta                                                    23

<210> SEQ ID NO 16
<211> LENGTH: 23
<212> TYPE: DNA
<213> ORGANISM: Artificial Sequence
<220> FEATURE:
<223> OTHER INFORMATION: PCR product in case of homologous
      recombination (Figure 4)

<400> SEQUENCE: 16
tgaaatcgat gggcccaaat gca                                                    23

<210> SEQ ID NO 17
<211> LENGTH: 23
<212> TYPE: DNA
<213> ORGANISM: Artificial Sequence
<220> FEATURE:
<223> OTHER INFORMATION: PCR product in case of homologous
      recombination (opposite strand of Sequence ID No: 16)
      (Figure 4)

<400> SEQUENCE: 17
tgcatttggg cccatcgatt tca                                                    23
```